(12) United States Patent
Hiura et al.

(10) Patent No.: US 9,617,202 B2
(45) Date of Patent: Apr. 11, 2017

(54) METHOD FOR PRODUCING 1,5-PENTANEDIAMINE

(71) Applicant: AJINOMOTO CO., INC., Tokyo (JP)

(72) Inventors: Takehiro Hiura, Kanagawa (JP);
Akifumi Hasegawa, Kanagawa (JP);
Takehiko Chikamori, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/048,287

(22) Filed: Feb. 19, 2016

(65) Prior Publication Data

US 2016/0168075 A1   Jun. 16, 2016

Related U.S. Application Data

(63) Continuation of application No. PCT/JP2014/071796, filed on Aug. 20, 2014.

(30) Foreign Application Priority Data

Aug. 23, 2013   (JP) .................................. 2013-173861

(51) Int. Cl.
C07C 209/86   (2006.01)

(52) U.S. Cl.
CPC .................................. C07C 209/86 (2013.01)

(58) Field of Classification Search
CPC .................................................. C07C 209/86
See application file for complete search history.

(56) References Cited

U.S. PATENT DOCUMENTS

| 5,863,438 A * | 1/1999 | Katzakian, Jr. ........ B01J 39/046 210/674 |
| 5,880,313 A | 3/1999 | Zaima et al. | |

| 2011/0045162 A1 | 2/2011 | Crombez et al. |
| 2012/0295317 A1 | 11/2012 | Schroder et al. |
| 2015/0344405 A1 | 12/2015 | Hiura et al. |

FOREIGN PATENT DOCUMENTS

| JP | 62-080237 | 4/1987 |
| JP | 11-152246 | 6/1999 |
| JP | 2001-335315 | 12/2001 |
| JP | 2004-208646 | 7/2004 |
| JP | 2008-189661 | 8/2008 |
| JP | 2010-275516 | 12/2010 |
| JP | 2011-225554 | 11/2011 |
| JP | 2013-053080 | 3/2013 |
| JP | 2013-514069 | 4/2013 |

OTHER PUBLICATIONS

Machine translation for JP2004208646.*
Dionex Technical Note Jan. 1987 pp. 1-7.*
Dowex Ion Exchange Resins "Fundamentals of Ion exchange", Jun. 2000, p. 1-9.*
International Search Report and Written Opinion for PCT Patent App. No. PCT/JP2014/071796 (Oct. 28, 2014) with English language translation of the Search Report.

* cited by examiner

*Primary Examiner* — Sudhakar Katakam
*Assistant Examiner* — Ana Z Muresan
(74) *Attorney, Agent, or Firm* — Shelly Guest Cermak; Cermak Nakajima & McGowan LLP

(57) ABSTRACT

A simple and efficient method for producing 1,5-pentanediamine in a free form is provided. The method for producing 1,5-pentanediamine in a free form from a salt of 1,5-pentanediamine includes a step of adsorbing 1,5-pentanediamine in a free form onto a column of an ion exchange resin by applying a solution of salt of 1,5-pentanediamine to the column of the ion exchange resin, and a step of eluting a solution of the 1,5-pentanediamine in a free form from the ion exchange resin by applying an eluent solution to the column of the ion exchange resin onto which the 1,5-pentanediamine in a free form is absorbed.

6 Claims, 13 Drawing Sheets

METHOD FOR PRODUCING 1,5-PENTANEDIAMINE

This application is a Continuation of, and claims priority under 35 U.S.C. §120 to, International Application No. PCT/JP2014/071796, filed Aug. 20, 2014, and claims priority therethrough under 35 U.S.C. §119 to Japanese Patent Application No. 2013-173861, filed Aug. 23, 2013, the entireties of which are incorporated by reference herein.

BACKGROUND OF THE INVENTION

Field of the Invention

The present invention relates to a method for producing 1,5-pentanediamine (hereinafter, may be referred to as "1,5-PD").

Brief Description of the Related Art 1,5-PD is a substance that is predicted to be in a demand as a resin raw material, such as a polyamide resin or a pharmaceutical intermediate. Since 1,5-PD can be produced from a non-petroleum-based raw material, 1,5-PD has attracted attention in industry for its value in reducing environmental load.

Conventionally, purified 1,5-PD has been produced by a method of thermal decomposition of 1,5-PD carbonate or an alkali treatment of 1,5-PD hydrochloride (Japanese Patent Application Laid-Open No. 2010-275516, Japanese Patent Application Laid-Open No. 2013-53080, and Japanese Patent Application Laid-Open No. 2011-225554).

PCT Patent Application Publication No. 2013-514069 describes that cadaverine is biologically produced by extraction and phase-separation, and a cadaverine phase is purified by chromatography on an appropriate resin.

1,5-PD can be distilled as long as it is in a free form. Therefore, in Japanese Patent Application Laid-Open No. 2010-275516, it is necessary to decompose a salt of 1,5-PD at the very high temperature of 180° C. and crude 1,5-PD be then be purified under high pressure.

Accordingly, a simple and efficient method of obtaining purified 1,5-PD in a free form is desirable.

SUMMARY OF THE INVENTION

It is an aspect of the present invention to provide a simple and efficient method for producing 1,5-PD in a free form.

It has been found that when a salt of 1,5-PD is adsorbed on and eluted from an ion exchange resin, 1,5-PD in a free form can be simply and efficiently produced.

It is an aspect of the present invention to provide a method for producing 1,5-pentanediamine in a free form from a salt of 1,5-pentanediamine comprising applying a solution of a salt of 1,5-pentanediamine to an ion exchange resin column thereby allowing adsorption of 1,5-pentanediamine in a free form onto the column applying; and applying an eluent solution to the column, thereby eluting a solution of the 1,5-pentanediamine in a free form from the column.

It is a further aspect of the present invention to provide the method as described above, wherein the eluent solution is applied in an upflow mode to the column.

It is a further aspect of the present invention to provide the method as described above, wherein the eluent solution is applied in a downflow mode to the column.

It is a further aspect of the present invention to provide the method as described above, wherein the ion exchange resin is a weakly acidic cation exchange resin.

It is a further aspect of the present invention to provide the method as described above, wherein in step A), the solution of the salt of 1,5-pentanediamine is applied in a downflow mode to the column.

It is a further aspect of the present invention to provide the method as described above, wherein the solution of the salt of 1,5-pentanediamine has a pH of 3 to 10.

It is a further aspect of the present invention to provide the method as described above, wherein the salt of 1,5-pentanediamine is a hydrochloride or a sulfate.

It is a further aspect of the present invention to provide the method as described above, wherein the solution of the salt of 1,5-pentanediamine has a temperature of 15 to 60° C.

It is a further aspect of the present invention to provide the method as described above, wherein the eluent used in the elution step is sodium hydroxide or potassium hydroxide.

It is a further aspect of the present invention to provide the method as described above, wherein the eluent solution has a temperature of 15 to 60° C.

It is a further aspect of the present invention to provide the method as described above, wherein the eluent solution has a concentration of 0.5 N to 4 N.

It is a further aspect of the present invention to provide the method as described above, wherein the eluent solution has a concentration of 1 N or lower.

According to the present invention, 1,5-PD in a free form can be simply and efficiently produced from a salt of 1,5-PD.

DESCRIPTION OF THE PREFERRED EMBODIMENTS

Figure 1:
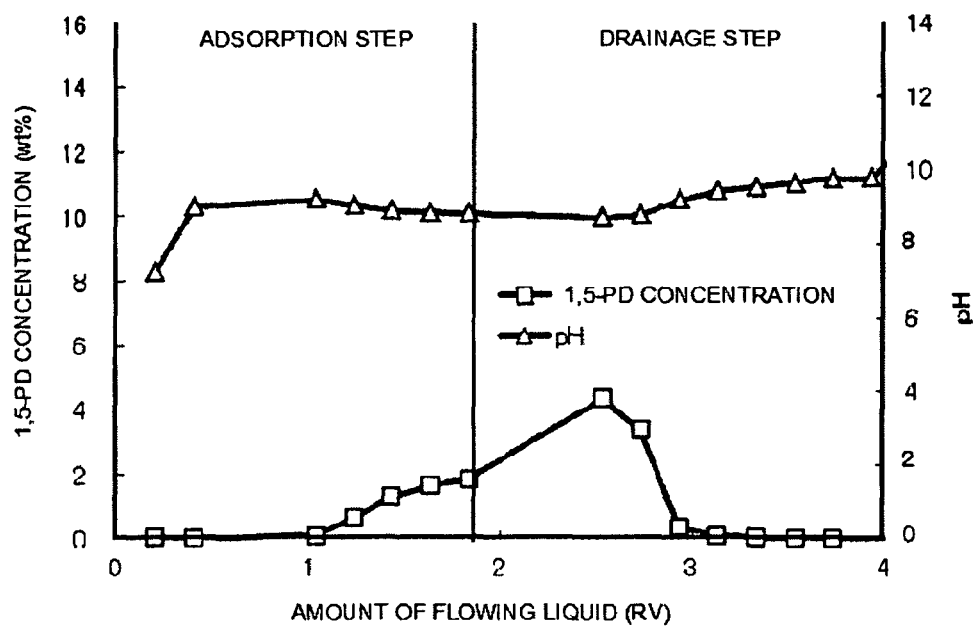
FIG. 1 shows an adsorption curve of 1,5-PD, which illustrates the results when applying a 1,5-PD hydrochloride solution to a strongly acidic cation exchange resin in a downflow mode (Example 1).

A method for producing 1,5-pentanediamine in a free form from a salt of 1,5-pentanediamine includes an adsorption step of adsorbing 1,5-pentanediamine in a free form onto an ion exchange resin column by applying a solution of the salt of 1,5-pentanediamine to the ion exchange resin column; and an elution step of eluting a solution of the 1,5-pentanediamine in a free form from the ion exchange resin by applying an eluent solution to the ion exchange resin column on which the 1,5-pentanediamine in a free form is adsorbed.

1,5-PD in a free form can be simply and efficiently produced from a salt of 1,5-PD by the method described above.

1,5-Pentanediamine (1,5-PD, 1,5-pentadiamine, chemical formula: $H_2N(CH_2)_5NH_2$) can also be referred to by its common name "cadaverine".

The phrase "salt of 1,5-pentanediamine" represents a salt formed from 1,5-PD and an acid. The salt of 1,5-PD is an intermediate during the production of 1,5-PD, and various types of salts are publicly known (for example, see Japanese Patent Application Laid-Open No. 2010-275516 and Japanese Patent Application Laid-Open No. 2013-53080). The type of salt is not particularly limited, and may be a monovalent or a divalent salt. The type of acid forming a salt with 1,5-PD may be an inorganic or organic acid, and may be a monovalent, divalent, or higher valency acid. Examples of the acid include hydrochoric acid, sulfuric acid, nitric acid, carbonic acid, carboxylic acid, phosphoric acid, and sulfonic acid. Examples of carboxylic acid include formic acid, acetic acid, adipic acid, glutaric acid, succinic acid, and sebacic acid. Particular examples of the salt of 1,5-PD include a hydrochloride or sulfate of 1,5-PD.

The method for producing the salt of 1,5-PD is not particularly limited. For example, a hydrochloride/sulfate of 1,5-PD can be produced as follows.

Since Lys hydrochloride or Lys sulfate is used as a raw material in an enzymatic reaction in which Lys is decarboxylated using lysine decarboxylase, hydrochloric acid or sulfuric acid that is derived from the raw material forms a salt with 1,5-PD to produce a hydrochloride or sulfate of 1,5-PD.

In the enzymatic reaction in which Lys is decarboxylated using lysine decarboxylase, hydrochloric acid or sulfuric acid to be added to a reaction solution forms a salt with 1,5-PD to produce a hydrochloride or sulfate of 1,5-PD.

The salt of 1,5-PD may be a salt produced from 1,5-PD produced by a fermentation process.

The phrase "1,5-pentanediamine in a free form" means 1,5-pentanediamine that is produced by demineralization of a salt of 1,5-PD and does not have a salt form.

The ion exchange resin used in the adsorption step and the elution step is not particularly limited, and may be selected depending on the acid that forms a salt with 1,5-PD. For example, when the salt is a hydrochloride or sulfate of 1,5-PD, a strongly acidic cation exchange resin (S-CER) or a weakly acidic cation exchange resin (W-CER) can be used, and W-CER is a particular example since elution at high exchange capacity and high efficiency is possible. Examples of other available ion exchange resins may include a resin having a carboxylic acid group as an exchange group, and a resin having a sulfonic acid group as an exchange group.

Examples of "strongly acidic cation exchange resin" may include resins having a sulfonic acid group and the like as an exchange group.

Examples of "weakly acidic cation exchange resin" may include resins having a carboxylic acid group, a phosphonic acid group, a phosphinic acid group, a phenoxide group, and an arsenous acid group as an exchange group.

Herein, "upflow" means that a resin column (resin tower) is positioned vertically or obliquely, and a liquid is applied to the lower portion of the resin column (resin tower) and drawn from the upper portion of the resin column (resin tower), so that the liquid flows through the resin column (resin tower) in a direction opposite to the gravity.

In contrast, "downflow" means that a resin column (resin tower) is positioned vertically or obliquely, and a liquid is applied to the upper portion of the resin column (resin tower) and drawn from the lower portion of the resin column (resin tower), so that the liquid flows through the resin column (resin tower) in the direction of gravity or a direction in accordance with gravity.

In the elution step, a liquid may be applied in the upflow or downflow mode. A high concentration of 1,5-PD can be collected by applying in the upflow mode as compared with in the downflow mode. By applying in the upflow mode, the exchange efficiency with the eluent can be also dramatically improved, and a solution having a high concentration of 1,5-PD in a free form that is minimally contaminated with the eluent can be obtained.

In the elution step, when the liquid is applied in the upflow mode, an auxiliary raw material including the eluent can be decreased, and a high concentration of 1,5-PD can be collected. Therefore, the energy required to obtain 1,5-PD in a free form can be decreased. Furthermore, the eluent can be prevented from contaminating the solution of 1,5-PD in a free form, and therefore the purity of the solution of 1,5-PD in a free form can be increased.

In the adsorption step, the liquid may be applied in the upflow or downflow mode. In terms of improved adsorption efficiency, the downflow mode is preferred. Onset of leakage of 1,5-PD into a flowing liquid is largely suppressed by applying in the downflow mode as compared with in the upflow mode, and adsorption is more efficient.

The pH of the solution of salt of 1,5-pentanediamine is generally 3 to 10, 4 to 9, or 5 to 8. As the solvent of the solution, water is generally used.

The temperature of the solution of salt of 1,5-pentanediamine can be 15 to 60° C.

An increase in the temperature can improve the adsorption efficiency. Therefore, the solution temperature can be 15° C. or higher, 20° C. or higher, or 30° C. or higher. However, when the solution temperature is too high, the amount of energy to be utilized increases, which is industrially disadvantageous. In addition, the life span of ion exchange resin is shortened. Therefore, the solution temperature can be 60° C. or lower, 50° C. or lower, or 40° C. or lower.

The eluent used in the elution step is not particularly limited as long as it is an alkali substance. Examples of the eluent may include sodium hydroxide, potassium hydroxide, and ammonia. When an eluent having high alkalinity, such as sodium hydroxide and potassium hydroxide, is used, the elution efficiency can be improved. Therefore, a solution of 1,5-PD in a free form that is prevented from being contaminated with the eluent can be obtained. When ammonia is used as an eluent, it can contaminate the solution of 1,5-PD in a free form. However, ammonia can be separated from the solution of 1,5-PD in a free form by a subsequent distillation. Therefore, the use of ammonia as the eluent is disadvantageous in terms of energy as compared with use of sodium hydroxide or potassium hydroxide, but has no problem for use. As a solvent of the eluent solution, water is generally used.

When elution is performed in the upflow mode, the concentration of the eluent can be 0.5 N to 4 N, or 1 N to 4 N. By the elution in the upflow mode, the concentration of 1,5-PD in the eluent solution can be increased with an increase in the concentration of the eluent. Therefore, this elution is advantageous in terms of energy.

In particular, even when the concentration of sodium hydroxide is increased in the elution in the upflow mode, breakthrough of the eluent does not occur. The concentration of 1,5-PD to be eluted increases with an increase in the concentration of sodium hydroxide. Therefore, an eluent concentration of 2N or more sodium hydroxide can be used.

When elution is performed in the downflow mode, the concentration of the eluent solution can be 1 N or less, or 0.5 N or less. When the concentration of the eluent is decreased in the elution in the downflow mode, the elution efficiency can be improved. A solution of 1,5-PD in a free form in which contamination with the eluent is suppressed can be collected.

The temperature of the eluent solution can be 15 to 60° C. When the temperature of the eluent solution is increased, a solution of 1,5-PD in a free form with high purity that is not contaminated with the eluent can be more efficiently obtained. Therefore, the solution temperature can be 15° C. or higher, 20° C. or higher, or 30° C. or higher. However, when the solution temperature is too high, the amount of energy to be utilized increases, which is industrially disadvantageous. In addition, the life span of the ion exchange resin is shortened. Therefore, the solution temperature can be 60° C. or lower, 50° C. or lower, or 40° C. or lower.

The elution step may be optionally performed a plurality of times by linkage of resin columns used for the elution. As a result, a leaked eluent component is used as the eluent in a next column. Therefore, the eluent can be utilized at high efficiency.

In order to increase the purification efficiency, the adsorption step through the ion exchange resin column in the downflow mode or the distillation operation may be optionally performed after the elution step through the ion exchange resin column. As the ion exchange resin, one that is the same as used in the adsorption step and the elution step can be used.

In production of the solution of 1,5-PD in a free form, a process at high efficiency and high degree of purification is established. A non-limiting example of a process suitable for industrialization is described below.

(1) Preparation of test solution; Water is added to a solution of 100% 1,5-PD obtained through distillation, and 35% hydrochloric acid is then added for neutralization to prepare a solution of 7.5% by weight 1,5-PD hydrochloride with a pH of 7.

For general industrial production, use of a solution in which lysine hydrochloride is dissolved followed by enzymatic decarboxylation, or the like is considered.

(2) Pretreatment of resin; A resin tower is filled with a weakly acidic cation exchange resin, 10 RV of 0.2N HCl, 10 RV of ultrapure water, 10 RV of 1N NaOH, and 10 RV of ultrapure water are applied to the resin tower to regenerate the resin as a $Na^+$ type resin.

For general industrial production, a resin that adsorbs or elutes 1,5-PD once can be used as is without initial pretreatment before each use. Specifically, substances adsorbed onto the resin in each step include 1,5-PD in a free form during the adsorption step, and a cation of alkali substance used as the eluent, such as a sodium ion and a potassium ion, during the elution step. Thus, the resin may not be subjected to the pretreatment again for transfer to a next cycle.

(3) Adsorption step; The solution of 1,5-PD hydrochloride prepared in (1) is applied in a downflow mode (the solution is applied to the upper portion of the resin tower and drawn from the lower portion) to the resin pretreated in (2) while 257 g of L-Resin is loaded. Thus, 1,5-PD is adsorbed onto the resin. After applying the test solution, about 4 RV of ultrapure water is applied to the resin tower by a flowing method that is the same as in the adsorption step to remove unabsorbed 1,5-PD from the resin tower.

This test presupposes that an operation is performed at high loading for the resin exchange capacity to use the resin exchange capacity to the maximum, and breakthrough of 1,5-PD occurs in the latter half of the adsorption step.

For general industrial production, an adsorption loading close to the exchange capacity is general. In an operation process, leakage can be decreased to the minimal by linkage of resin towers used for adsorption.

(4) Elution step; 2N NaOH is applied to the resin tower that adsorbs 1,5-PD in (3) in an upflow mode (the solution is supplied to the lower portion of the resin tower and drawn from the upper portion), and elution of 1,5-PD and breakthrough of sodium are each confirmed.

For general industrial production, elution is completed just before onset of breakthrough of the eluent. In the operation process, a leaked eluent component is used as an eluent in a next tower by linkage of resin towers used for elution. Therefore, the eluent can be utilized at high efficiency.

EXAMPLES

Hereinafter, the present invention will be more specifically described with reference to the following non-limiting Examples.

Example 1 Selection of Cation Exchange Resin for Removal of 1,5-PD Counter Ion

Selection of Strongly Acidic Cation Exchange Resin and Weakly Acidic Cation Exchange Resin in Adsorption Step (1) Preparation of test solution; Water was added to a solution of 100% 1,5-PD obtained through distillation, and 35% hydrochloric acid was then added for neutralization to prepare a solution of 8% by weight 1,5-PD hydrochloride with a pH of 7.

(2) Pretreatment of resin; A resin tower was filled with each of a strongly acidic cation exchange resin (DIAION SK-1B available from Mitsubishi Chemical Corporation, exchange group: sulfonic acid group) and a weakly acidic cation exchange resin (Lewatit CNP80WS available from LANXESS, exchange group: carboxylic acid group), and 10 RV (Resin Volume) of 0.2N HCl, 10 RV of ultrapure water, 10 RV of 1N NaOH, and 10 RV of ultrapure water were applied to the resin tower to regenerate the resin as a $Na^+$ type resin.

(3) Examination of adsorption amount; The solution of 1,5-PD hydrochloride prepared in (1) was applied in a downflow mode (the solution was supplied to an upper portion of the resin tower and drawn from a lower portion) while loading 216 g/L-Resin and 250 g/L-Resin to the respective resins. Thus, 1,5-PD was adsorbed on each of the resins. After applying the test solution, ultrapure water was applied to each of the resin towers to remove unabsorbed 1,5-PD from each of the resin towers.

2N NaOH was applied to each of the resin towers until the elution of 1,5-PD terminated. Thus, the amount of 1,5-PD adsorbed on each of the resins was confirmed.

FIG. 1 shows an adsorption curve of 1,5-PD when using the strongly acidic cation exchange resin.

Figure 2:
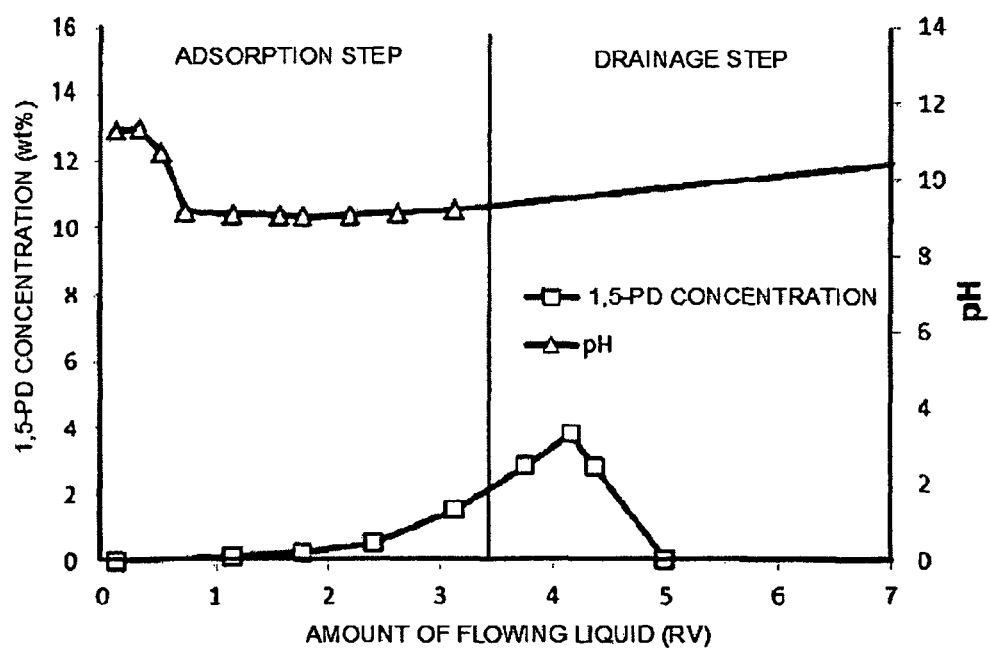
FIG. 2 shows an adsorption curve of 1,5-PD, which illustrates the results when applying a 1,5-PD hydrochloride solution to a weakly acidic cation exchange resin in the downflow mode (Example 1).

FIG. 2 shows an adsorption curve of 1,5-PD when using the weakly acidic cation exchange resin.

Adsorption of 1,5-PD on each of the strongly acidic cation exchange resin and the weakly acidic cation exchange resin is possible, and the adsorption amounts thereof are 56 g/L-Resin and 200 g/L-Resin, respectively.

W-CER generally has characteristics of weak adsorption power as compared with S-CER. However, it is found that W-CER makes it possible to adsorb 1,5-PD with decreased leakage similarly to S-CER.

Example 2 Selection of Cation Exchange Resin for Removal of 1,5-PD Counter Ion

Selection of Strongly Acidic Cation Exchange Resin and Weakly Acidic Cation Exchange Resin in Elution Step (1) Preparation of test solution; Water was added to a solution of 100% 1,5-PD obtained through distillation, and 35% hydrochloric acid was then added for neutralization to prepare a solution of 8% by weight 1,5-PD hydrochloride with a pH of 7.

(2) Pretreatment of resin; A resin tower was filled with each of the strongly acidic cation exchange resin and the weakly acidic cation exchange resin, and 10 RV of 0.2N HCl, 10 RV of ultrapure water, 10 RV of 1N NaOH, and 10 RV of ultrapure water were applied to the resin tower to regenerate the resin as a $Na^+$ type resin.

(3) Examination of adsorption amount; The solution of 1,5-PD hydrochloride prepared in (1) was applied in a downflow mode (the solution was supplied to an upper portion of the resin tower and drawn from a lower portion) while loading 216 g/L-Resin and 250 g/L-Resin to the respective resins. Thus, 1,5-PD was adsorbed on each of the resins. After applying the test solution, ultrapure water was applied to each of the resin towers to remove unabsorbed 1,5-PD on each of the resins from each of the resin towers.

(4) 2N NaOH was applied to each of the resin towers in the downflow mode. Then, elution of 1,5-PD and breakthrough of sodium were confirmed.

Figure 3:
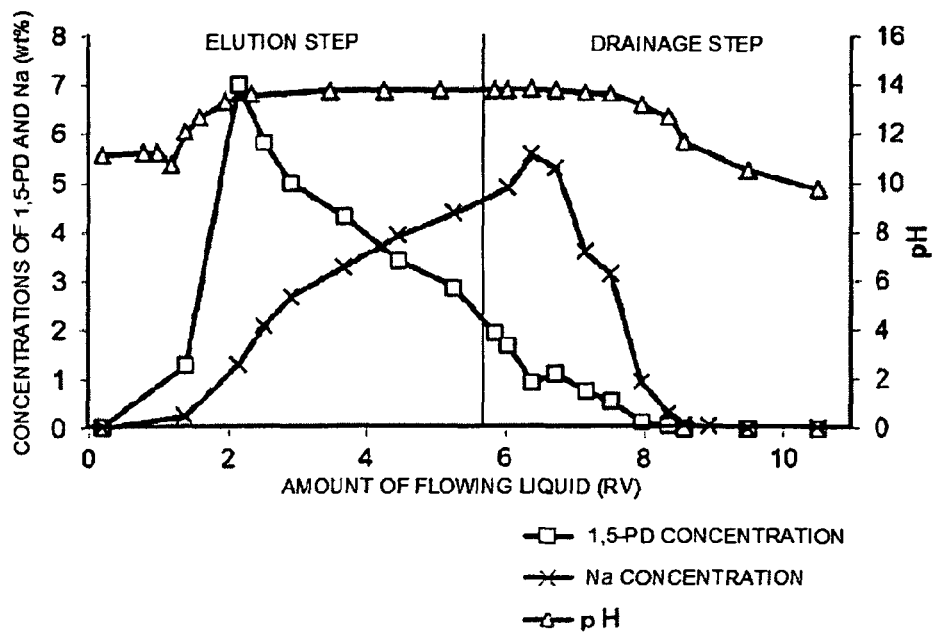
FIG. 3 shows an elution curve of 1,5-PD, which illustrates the results when applying a 1,5-PD hydrochloride solution to a strongly acidic cation exchange resin in the downflow mode (Example 2).

FIG. 3 shows an elution curve of 1,5-PD when using the strongly acidic cation exchange resin.

Figure 4:
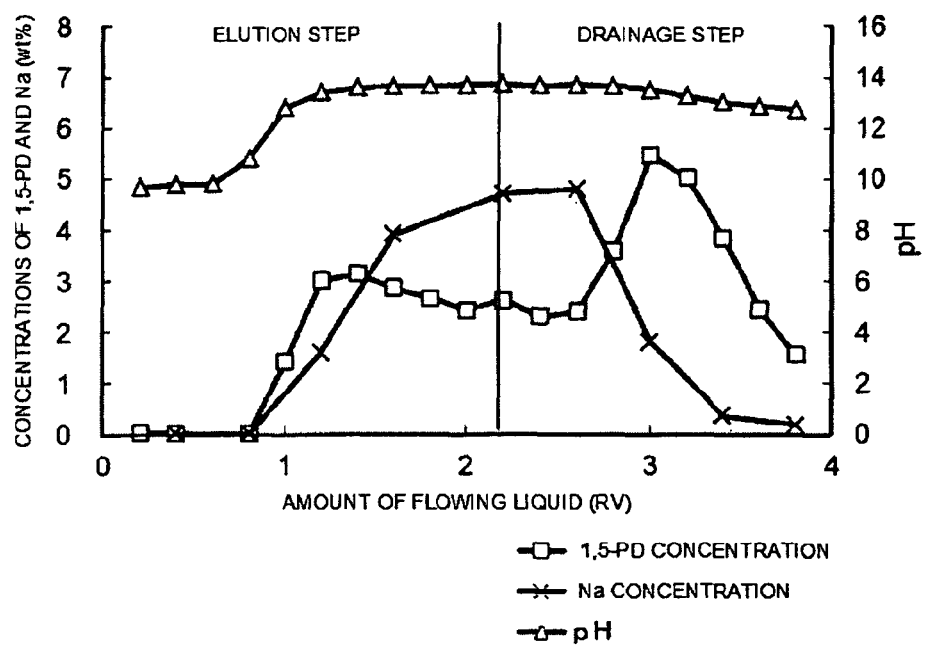
FIG. 4 shows an elution curve of 1,5-PD, which illustrates the results when applying a 1,5-PD hydrochloride solution to a weakly acidic cation exchange resin in the downflow mode (Example 2).

FIG. 4 shows an elution curve of 1,5-PD when using the weakly acidic cation exchange resin.

Elution of 1,5-PD from both the strongly acidic cation exchange resin and the weakly acidic cation exchange resin is possible. It is confirmed that in the strongly acidic cation exchange resin, elution of sodium starts with elution of 1,5-PD, and continues until the elution of 1,5-PD terminates, and in the weakly acidic cation exchange resin, elution of sodium terminates before the elution of 1,5-PD terminates.

W-CER generally has characteristics of weak adsorption power as compared with S-CER. It is found that when W-CER is used in elution of 1,5-PD adsorbed on the resin, the elution can proceed at high efficiency as compared with S-CER.

Example 3 Selection of pH Conditions for Adsorption of 1,5-PD on Weakly Acidic Cation Exchange Resin Selection of pH for 1,5-PD Solution Applied to Resin (1) Preparation of test solution; Water was added to a solution of 100% 1,5-PD obtained through distillation, and 35% hydrochloric acid was then added for neutralization to prepare i) a solution of 7.5% by weight 1,5-PD hydrochloride with a pH of 5 and ii) a solution of 7.5% by weight 1,5-PD hydrochloride with a pH of 7.

(2) Pretreatment of resin; A resin tower was filled with the weakly acidic cation exchange resin, and 10 RV of 0.2N HCl, 10 RV of ultrapure water, 10 RV of 1N NaOH, and 10 RV of ultrapure water were applied to the resin tower to regenerate the resin as a $Na^+$ type resin.

(3) Examination of adsorption amount; The two types of solution of 1,5-PD hydrochloride prepared in (1) were each applied in a downflow mode (the solution was supplied to an upper portion of the resin tower and drawn from a lower portion) while loading 250 g/L-Resin to the pretreated resin in (2). Thus, 1,5-PD was adsorbed on the resin. After applying the test solution, ultrapure water was applied to each of the resin towers to remove unabsorbed 1,5-PD from each of the resin towers.

2N NaOH was applied to each of the resin towers until the elution of 1,5-PD terminated. Thus, the amount of 1,5-PD adsorbed on each of the resins was confirmed.

Figure 5:
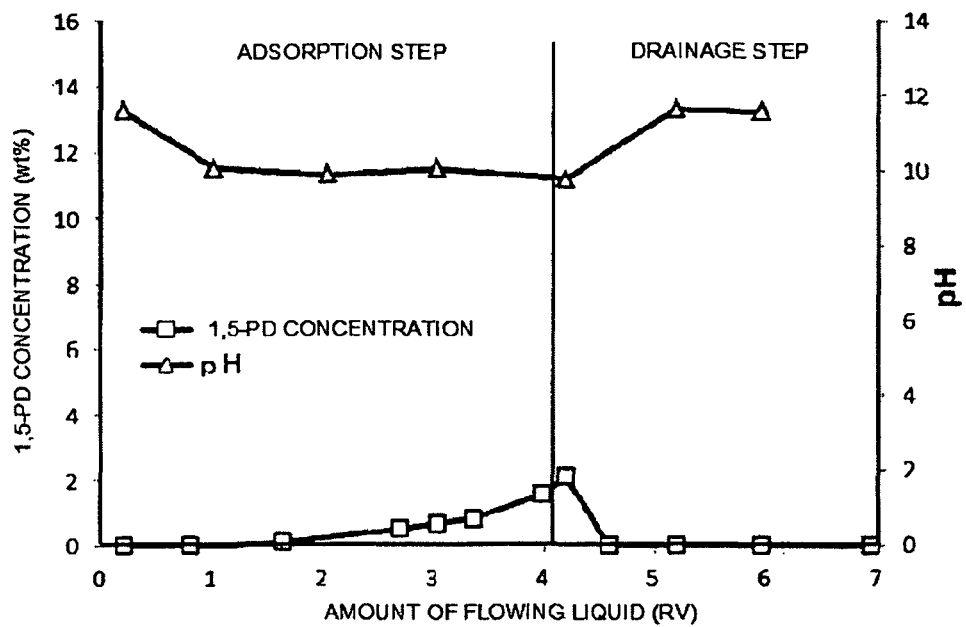
FIG. 5 shows an adsorption curve of 1,5-PD, which illustrates the results when applying 1,5-PD of pH 5 to a weakly acidic cation exchange resin in the downflow mode (Example 3).

FIG. 5 shows an adsorption curve of 1,5-PD when applying the 1,5-PD with a pH of 5 through the weakly acidic cation exchange resin.

Figure 6:
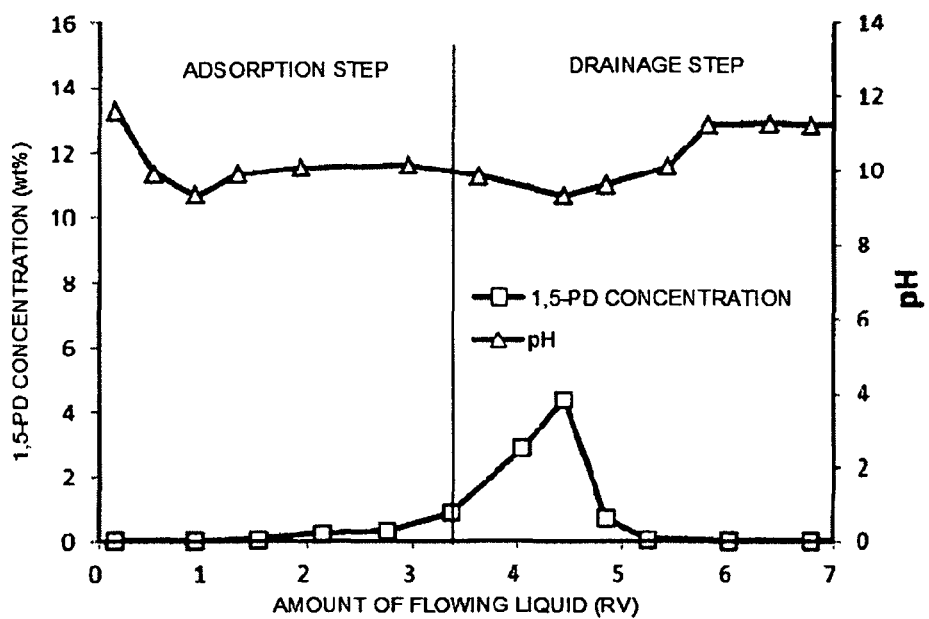
FIG. 6 shows an adsorption curve of 1,5-PD, which illustrates the results when applying 1,5-PD of pH 7 to a weakly acidic cation exchange resin in the downflow mode (Example 3).

FIG. 6 shows an adsorption curve of 1,5-PD when applying the 1,5-PD with a pH of 7 through the weakly acidic cation exchange resin.

The adsorption amounts of 1,5-PD in the cases are almost the same as 198 g/L-resin and 212 g/L-resin, respectively, at a pH of 5 to 7. Thus, it is confirmed that adsorption at a pH range of 5 to 7 is possible.

W-CER has such characteristics that W-CER cannot decompose a neutral salt such as NaCl and $Na_2SO_4$ and can be replaced with a base such as NaOH due to weak acidity. It is generally considered that 1,5-PD is likely to be adsorbed at or near neutral pH as compared with under acidity.

Example 4 Selection of 1,5-PD Counter Type

Selection of 1,5-PD Solution Counter Type Applied to Resin (1) Preparation of test solution; Water was added to a solution of 100% 1,5-PD obtained through distillation, and 35% hydrochloric acid or 98% sulfuric acid was then added for neutralization to prepare i) a solution of 7.5% by weight 1,5-PD hydrochloride with a pH of 7 and ii) a solution of 7.5% by weight 1,5-PD sulfate with a pH of 7.

(2) Pretreatment of resin; A resin tower was filled with the weakly acidic cation exchange resin, and 10 RV of 0.2N HCl, 10 RV of ultrapure water, 10 RV of 1N NaOH, and 10 RV of ultrapure water were applied to the resin tower to regenerate the resin as a $Na^+$ type resin.

(3) Examination of adsorption amount; The solutions of 1,5-PD hydrochloride and 1,5-PD sulfate prepared in (1) were each applied in a downflow mode (the solution was supplied to an upper portion of the resin tower and drawn from a lower portion) while loading 250 g/L-Resin to the pretreated resin in (2). Thus, 1,5-PD was adsorbed on the resin. After applying the test solution, ultrapure water was applied to each of the resin towers to remove unabsorbed 1,5-PD from each of the resin towers.

2N NaOH was applied to each of the resin towers until the elution of 1,5-PD terminated. Thus, the amount of 1,5-PD adsorbed on each of the resins was confirmed.

Figure 7:
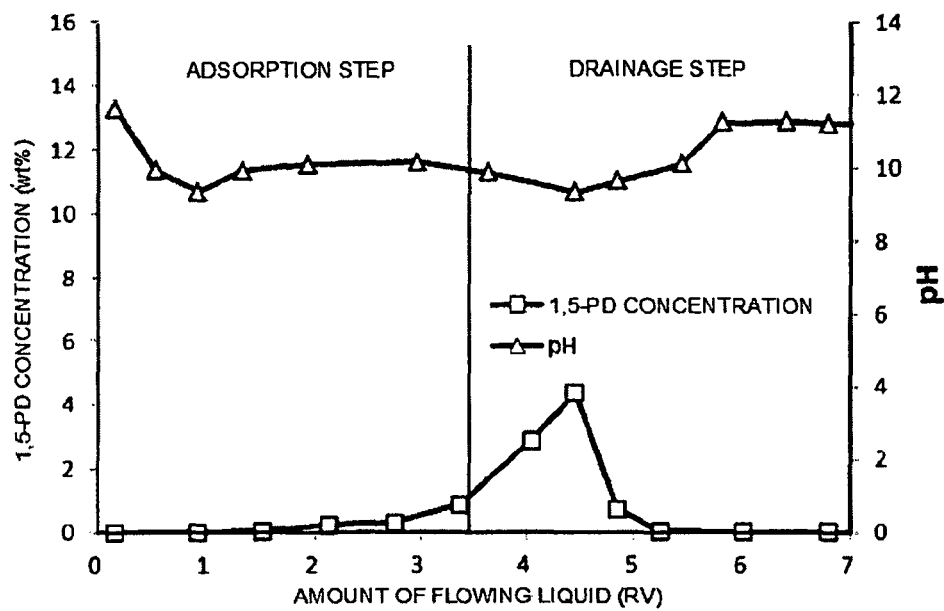
FIG. 7 shows an adsorption curve of 1,5-PD, which illustrates the results when applying a 1,5-PD hydrochloride solution to a weakly acidic cation exchange resin in the downflow mode (Example 4).

FIG. 7 shows an adsorption curve of 1,5-PD when applying the 1,5-PD hydrochloride solution through the weakly acidic cation exchange resin.

Figure 8:
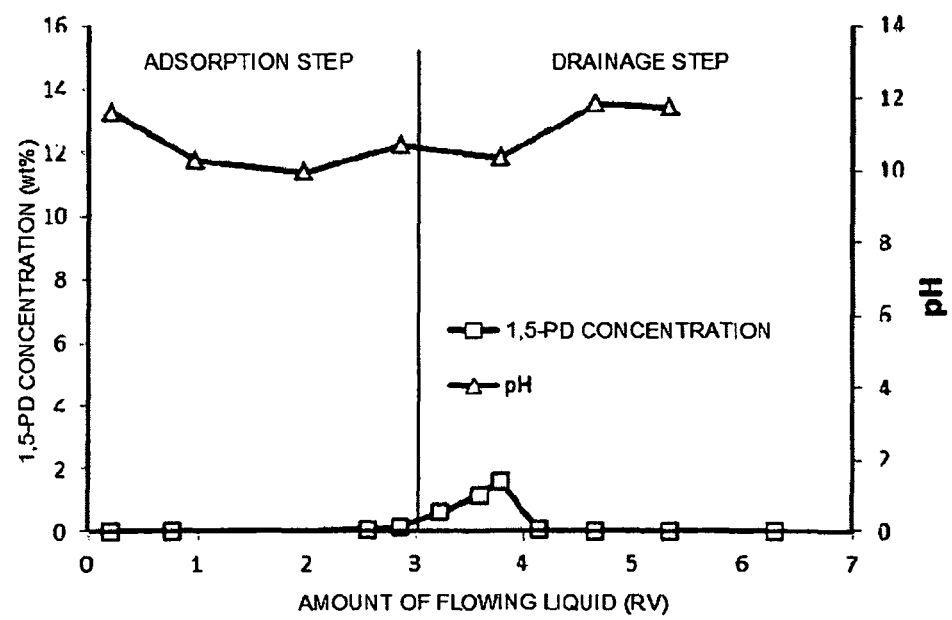
FIG. 8 shows an adsorption curve of 1,5-PD, which illustrates the results when applying a 1,5-PD sulfate solution to a weakly acidic cation exchange resin in the downflow mode (Example 4).

FIG. 8 shows an adsorption curve of 1,5-PD when applying the 1,5-PD sulfate solution through the weakly acidic cation exchange resin.

Both the 1,5-PD hydrochloride solution and the 1,5-PD sulfate solution are made possible to adsorb 1,5-PD on the resin, and the adsorption amounts are 212 g/L-Resin and 192 g/L-Resin, respectively.

Example 5 Selection of Adsorption Temperature

Selection of Temperature of 1,5-PD Solution Applied to Resin (1) Preparation of test solution; Water was added to a solution of 100% 1,5-PD obtained through distillation, and 35% hydrochloric acid was then added for neutralization to prepare a solution of 8% by weight 1,5-PD hydrochloride with a pH of 7.

(2) Pretreatment of resin; A resin tower was filled with the weakly acidic cation exchange resin, and 10 RV of 0.2N HCl, 10 RV of ultrapure water, 10 RV of 1N NaOH, and 10 RV of ultrapure water were applied to the resin tower to regenerate the resin as a $Na^+$ type resin.

(3) Examination of adsorption amount; The solution of 1,5-PD hydrochloride prepared in (1) and having a solution temperature of 20° C. or 40° C. was applied in a downflow mode (the solution was supplied to an upper portion of the resin tower and drawn from a lower portion) while loading 250 g/L-Resin to the pretreated resin in (2). Thus, 1,5-PD was adsorbed onto the resin. After applying the test solution, ultrapure water was applied to each of the resin towers to remove unabsorbed 1,5-PD from each of the resin towers.

2N NaOH was applied to each of the resin towers until the elution of 1,5-PD terminated. Thus, the amount of 1,5-PD adsorbed on each of the resins was confirmed.

Figure 9:
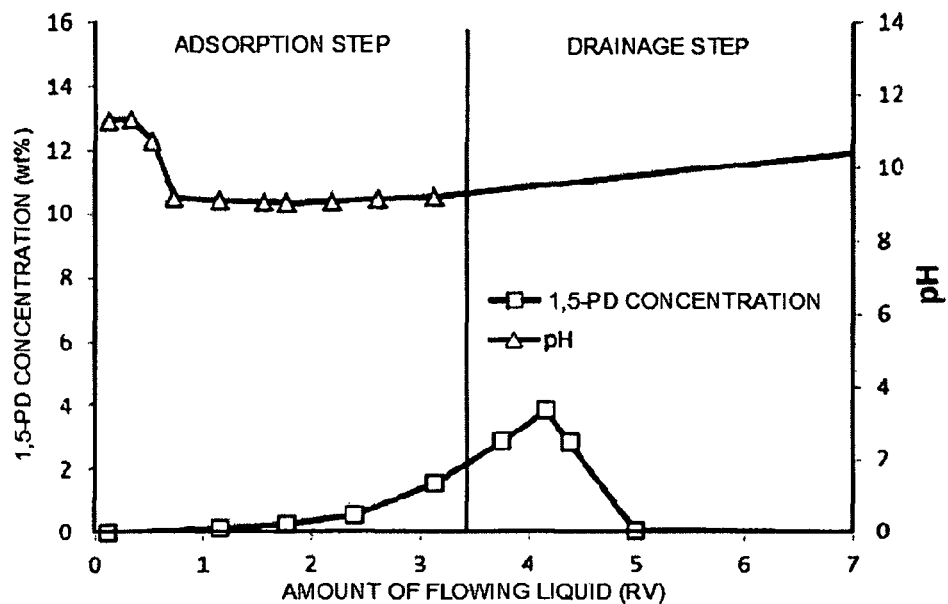
FIG. 9 shows an adsorption curve of 1,5-PD, which illustrates the results when applying a 1,5-PD hydrochloride solution having a solution temperature of 20° C. to a weakly acidic cation exchange resin in the downflow mode (Example 5).

FIG. 9 shows an adsorption curve of 1,5-PD when applying the 1,5-PD hydrochloride solution having a solution temperature of 20° C. through the weakly acidic cation exchange resin.

Figure 10:
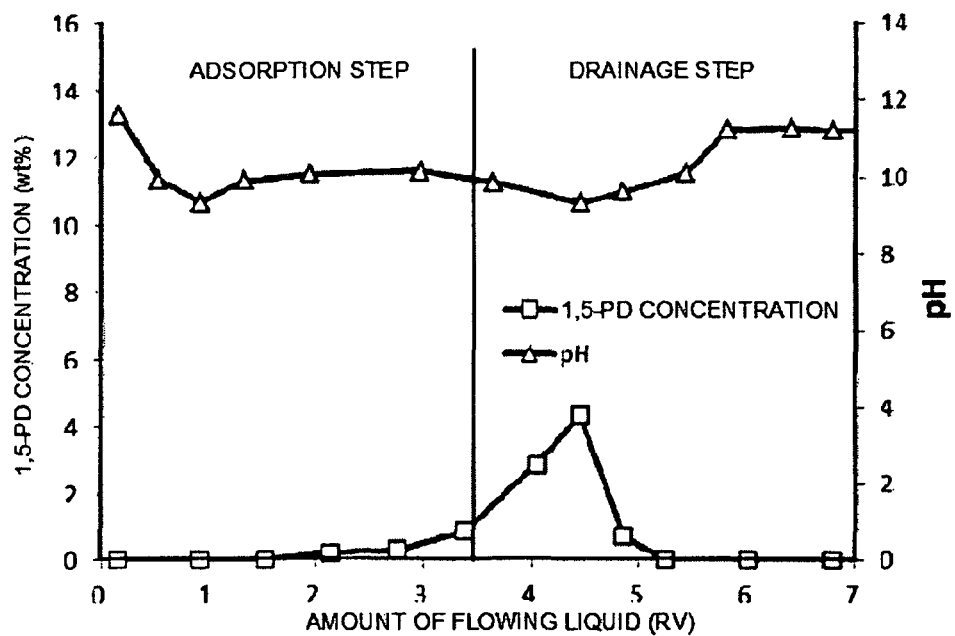
FIG. 10 shows an adsorption curve of 1,5-PD, which illustrates the results when applying a 1,5-PD hydrochloride solution having a temperature of 40° C. to a weakly acidic cation exchange resin in the downflow mode (Example 5).

FIG. 10 shows an adsorption curve of 1,5-PD that is a result when applying the 1,5-PD hydrochloride solution having a solution temperature of 40° C. through the weakly acidic cation exchange resin.

Adsorption of 1,5-PD on the resin at both 20° C. and 40° C. is possible, and the adsorption amounts are 195 g/L-Resin and 212 g/L-Resin, respectively. The onset of leakage of 1,5-PD into a flowing liquid is suppressed by adsorption at 40° C. as compared with that at 20° C.

The adsorption efficiency on the resin is generally improved by heating.

Example 6 Selection of Adsorption and Flowing Method

Selection of Flowing Method Through Resin (1) Preparation of test solution; Water was added to a solution of 100% 1,5-PD obtained through distillation, and 35% hydrochloric acid was then added for neutralization to prepare a solution of 8% by weight 1,5-PD hydrochloride with a pH of 7.

(2) Pretreatment of resin; A resin tower was filled with the weakly acidic cation exchange resin, and 10 RV of 0.2N HCl, 10 RV of ultrapure water, 10 RV of 1N NaOH, and 10 RV of ultrapure water were applied to the resin tower to regenerate the resin as a $Na^+$ type resin.

(3) Examination of adsorption amount; The 1,5-PD hydrochloride solution prepared in (1) was applied in a downflow mode (the solution was supplied to an upper portion of the resin tower and drawn from a lower portion) or in an upflow mode (the solution was supplied to the lower portion of the resin tower and drawn from the upper portion) while loading 250 g/L-Resin to the resin pretreated in (2). Thus, 1,5-PD was adsorbed on the resin. After applying the test solution, ultrapure water was applied to each of the resin towers by the flowing method that was the same as in the adsorption to remove unabsorbed 1,5-PD from each of the resin towers.

2N NaOH was applied to each of the resin towers until the elution of 1,5-PD terminated. Thus, the amount of 1,5-PD adsorbed on each of the resins was confirmed.

Figure 11:
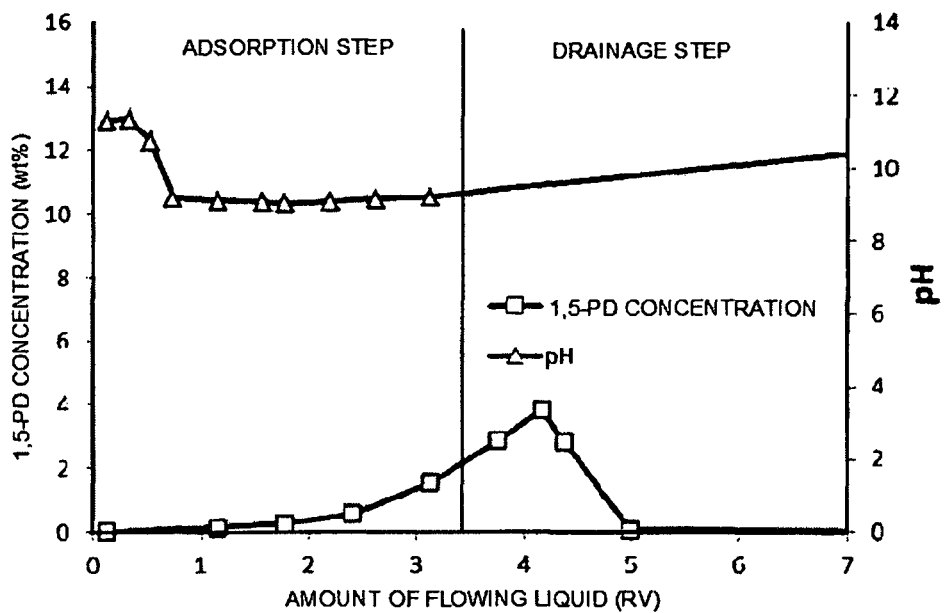
FIG. 11 shows an adsorption curve, which illustrates the results when applying a 1,5-PD hydrochloride solution to a weakly acidic cation exchange resin in the downflow mode (Example 6).

FIG. 11 shows an adsorption curve when applying the 1,5-PD hydrochloride solution through the weakly acidic cation exchange resin in the downflow mode.

Figure 12:
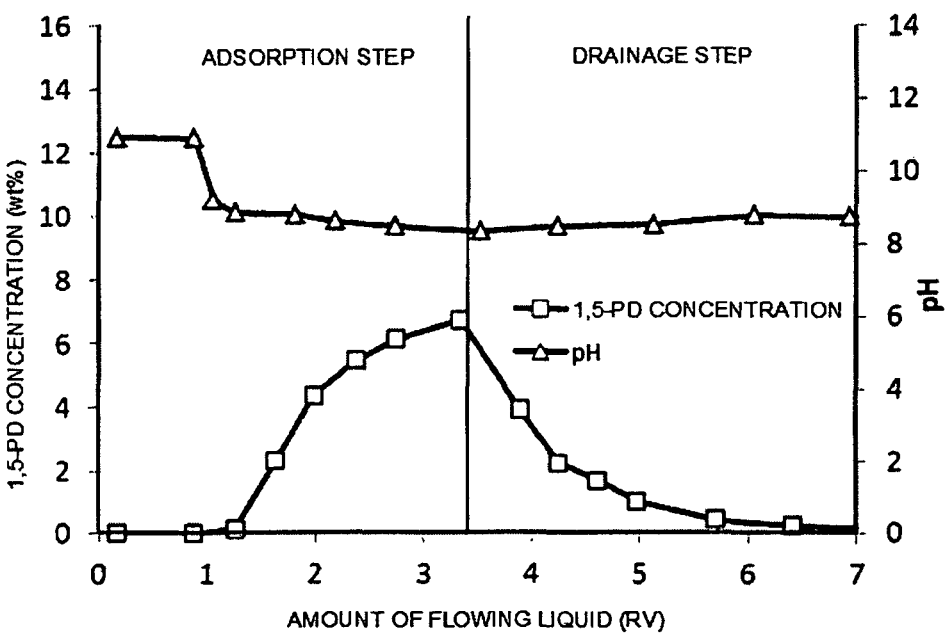
FIG. 12 shows an adsorption curve, which illustrates the results when applying a 1,5-PD hydrochloride solution to a weakly acidic cation exchange resin in an upflow mode (Example 6).

FIG. 12 shows an adsorption curve when applying the 1,5-PD hydrochloride solution through the weakly acidic cation exchange resin in the upflow mode.

The flowing methods in the downflow and upflow modes allow for adsorption of 1,5-PD onto the resin, and the adsorption amounts are 195 g/L-resin and 107 g/L-resin, respectively. The adsorption amount in the upflow mode is low. This is because the flowing terminated before completion of the adsorption. In contrast, the onset of leakage of 1,5-PD into a flowing liquid in the downflow mode is largely suppressed as compared with in the upflow mode, and adsorption at high efficiency in the downflow mode is made possible.

Example 7 Selection of Concentration of Eluent

Elution Step: Selection of Concentration of Eluent (1) Preparation of test solution; Water was added to a solution of 100% 1,5-PD obtained through distillation, and 35% hydrochloric acid was then added for neutralization to prepare a solution of 8% by weight 1,5-PD hydrochloride with a pH of 7.

(2) Pretreatment of resin; A resin tower was filled with the weakly acidic cation exchange resin, and 10 RV of 0.2N HCl, 10 RV of ultrapure water, 10 RV of 1N NaOH, and 10 RV of ultrapure water were applied to the resin tower to regenerate the resin as a $Na^+$ type resin.

(3) Examination of adsorption amount; The solution of 1,5-PD hydrochloride prepared in (1) was applied in a downflow mode (the solution was supplied to an upper portion of the resin tower and drawn from a lower portion) while loading 250 g/L-Resin to the pretreated resin in (2). Thus, 1,5-PD was adsorbed on the resin. After applying the test solution, ultrapure water was applied to each of the resin towers by the flowing method that was the same as in the adsorption to remove unabsorbed 1,5-PD from each of the resin towers.

(4) 2N, 1N, and 0.5N NaOH were applied to the resin towers, respectively. Then, elution of 1,5-PD and breakthrough of sodium were confirmed.

Figure 13:
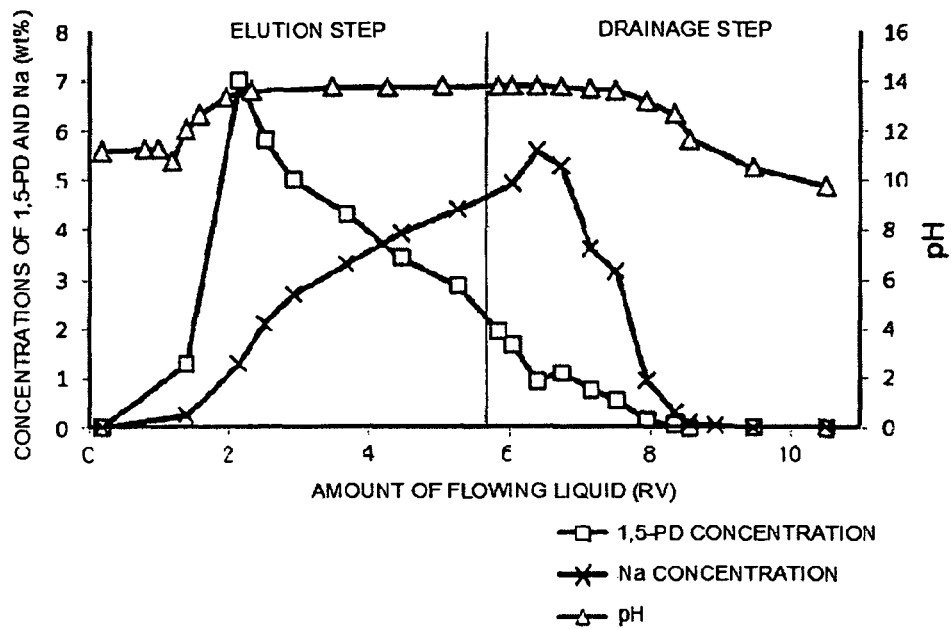
FIG. 13 shows an elution curve of 1,5-PD when a 1,5-PD hydrochloride solution was applied in the downflow mode to a weakly acidic cation exchange resin, ultrapure water was then applied to a resin tower to remove unabsorbed 1,5-PD, and 2N NaOH was then applied (Example 7).

FIG. 13 shows an elution curve in a case where the 1,5-PD hydrochloride solution was applied in the downflow mode to the weakly acidic cation exchange resin, ultrapure water was then applied to the resin tower to remove unabsorbed 1,5-PD, and 2N NaOH was applied.

Figure 14:
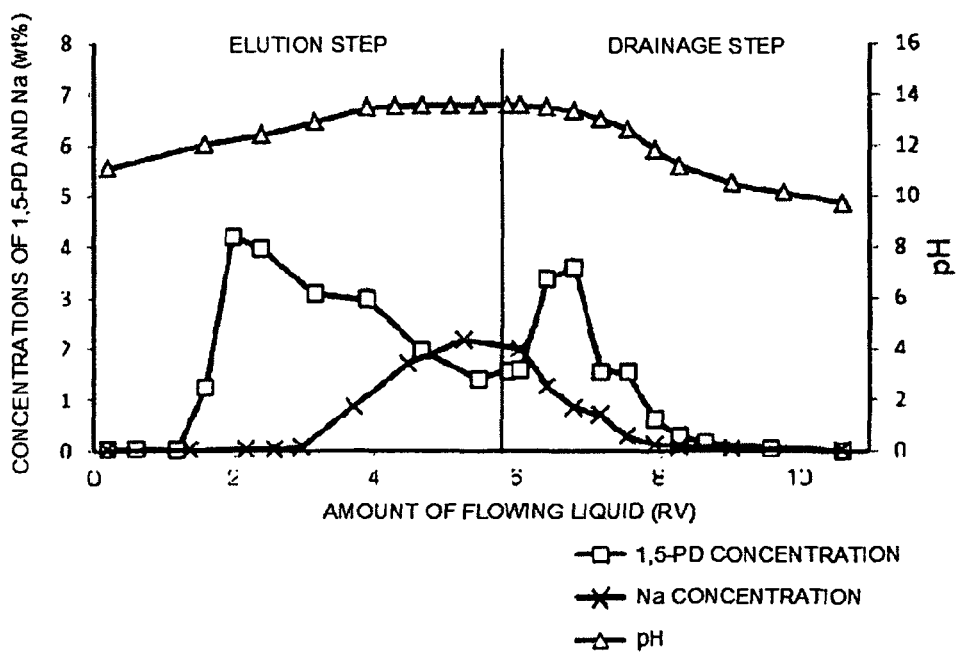
FIG. 14 shows an elution curve of 1,5-PD when a 1,5-PD hydrochloride solution was applied in the downflow mode to a weakly acidic cation exchange resin, ultrapure water was then applied to a resin tower to remove unabsorbed 1,5-PD, and 1N NaOH was then applied (Example 7).

FIG. 14 shows an elution curve when the 1,5-PD hydrochloride solution was applied in the downflow mode to the weakly acidic cation exchange resin, ultrapure water was then applied to the resin tower to remove unabsorbed 1,5-PD, and 1N NaOH was applied.

Figure 15:
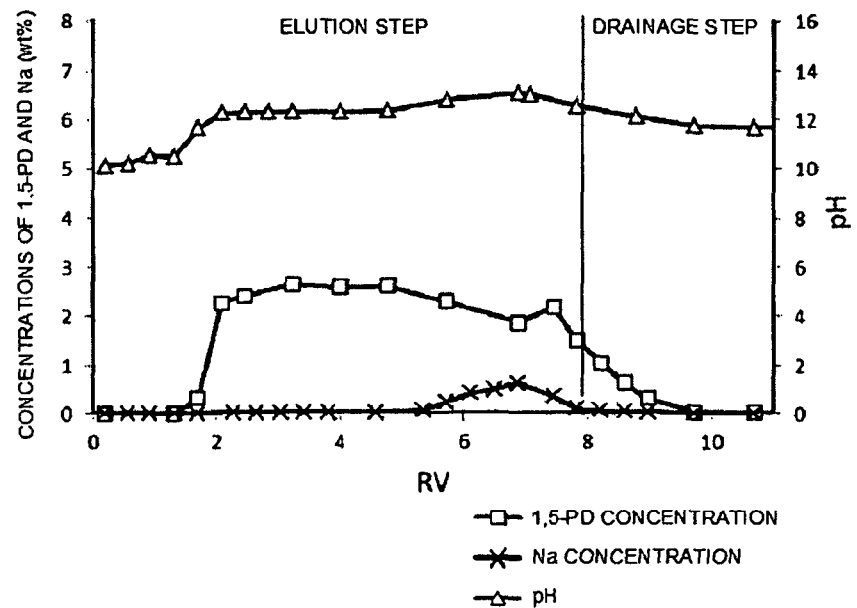
FIG. 15 shows an elution curve of 1,5-PD when a 1,5-PD hydrochloride solution was applied in the downflow mode to a weakly acidic cation exchange resin, ultrapure water was then applied to a resin tower to remove unabsorbed 1,5-PD, and 0.5 N NaOH was then applied (Example 7).

FIG. 15 shows an elution curve when the 1,5-PD hydrochloride solution was applied in the downflow mode to the weakly acidic cation exchange resin, ultrapure water was then applied to the resin tower to remove unabsorbed 1,5-PD, and 0.5N NaOH was applied.

In all the eluent concentrations, elution of 1,5-PD is possible. It is estimated that as the eluent concentration is higher, the concentration of 1,5-PD to be eluted increases. In contrast, as the eluent concentration is lower, the concentration of 1,5-PD to be eluted decreases. However, sodium as the eluent is efficiently used, and 1,5-PD in which contamination with sodium as the eluent is suppressed can be obtained.

Example 8 Selection of Elution and Flowing Method

Elution Step: Selection of Eluent Flowing Method (1) Preparation of test solution; Water was added to a solution of 100% 1,5-PD obtained through distillation, and 35% hydrochloric acid was then added for neutralization to prepare a solution of 12% by weight 1,5-PD hydrochloride with a pH of 5.

(2) Pretreatment of resin; A resin tower was filled with the weakly acidic cation exchange resin, and 10 RV of 0.2N HCl, 10 RV of ultrapure water, 10 RV of 1N NaOH, and 10 RV of ultrapure water were applied to the resin tower to regenerate the resin as a $Na^+$ type resin.

(3) Examination of adsorption amount; The solution of 1,5-PD hydrochloride prepared in (1) was applied in a downflow mode (the solution was applied to an upper portion of the resin tower and drawn from a lower portion) while loading 250 g/L-Resin to the pretreated resin in (2). Thus, 1,5-PD was adsorbed onto the resin. After applying the test solution, ultrapure water was applied to each of the resin towers by the flowing method that was the same as in the adsorption to remove unabsorbed 1,5-PD from each of the resin towers.

(4) 2N NaOH was applied to each of the resin towers in a downflow mode (the liquid was supplied to an upper portion of the resin tower and drawn from a lower portion) or an upflow mode (the liquid was supplied to the lower portion of the resin tower and drawn from the upper portion), and elution of 1,5-PD and breakthrough of sodium were each confirmed.

Figure 16:
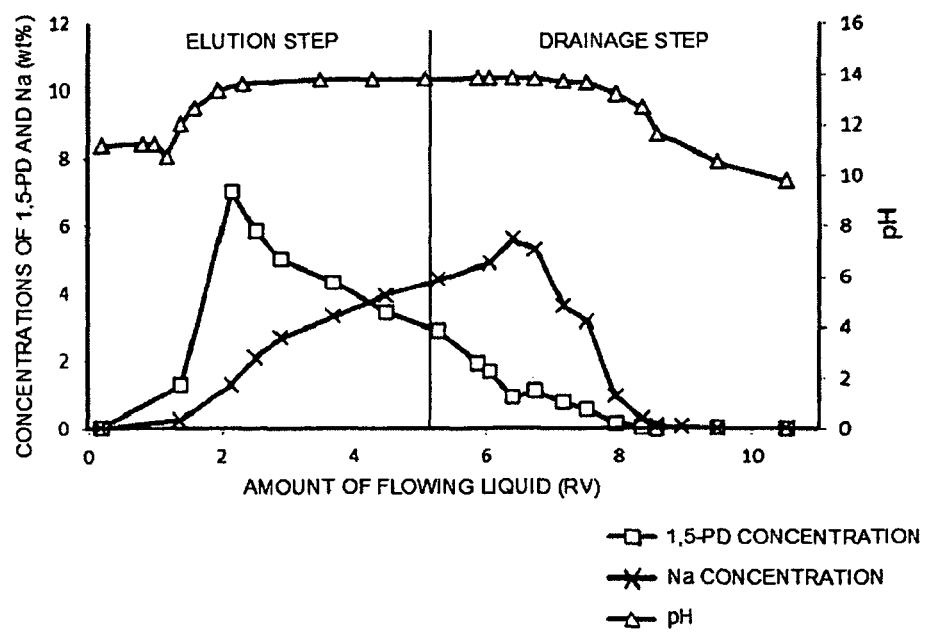
FIG. 16 shows an elution curve when a 1,5-PD hydrochloride solution was applied in the downflow mode to a weakly acidic cation exchange resin, ultrapure water was then applied to a resin tower to remove unabsorbed 1,5-PD, and 2N NaOH was then applied in the downflow mode (Example 8).

FIG. 16 shows an elution curve when the 1,5-PD hydrochloride solution was applied in the downflow mode to the weakly acidic cation exchange resin, ultrapure water was then applied to the resin tower to remove unabsorbed 1,5-PD, and 2N NaOH was applied in the downflow mode.

Figure 17:
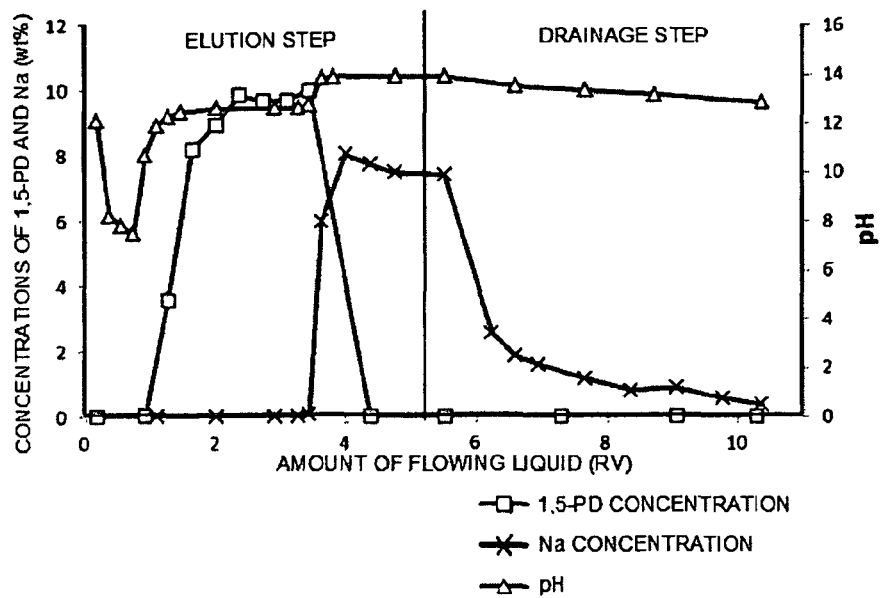
FIG. 17 shows an elution curve when a 1,5-PD hydrochloride solution was applied in the downflow mode to a weakly acidic cation exchange resin, ultrapure water was then applied to a resin tower to remove unabsorbed 1,5-PD, and 2N NaOH was then applied in an upflow mode (Example 8).

FIG. 17 shows an elution curve when the 1,5-PD hydrochloride solution was applied in the downflow mode to the weakly acidic cation exchange resin, ultrapure water was then applied to the resin tower to remove unabsorbed 1,5-PD, and 2N NaOH was applied in the upflow mode.

In both the eluent flowing modes, a counter ion forming an ionic bond can be separated, and therefore elution of 1,5-PD is possible. In the downflow mode, breakthrough of sodium starts with onset of elution of 1,5-PD. In contrast, in the upflow mode, elution of 1,5-PD is almost completed, and eluent of sodium then starts. Therefore, in the upflow mode, a solution of 1,5-PD in a free form in which the concentration of 1,5-PD is high and contamination with the eluent is suppressed can be obtained.

Example 9 Selection of Eluent

Elution Step: Selection of Alkali Type of Eluent (1) Preparation of test solution; Water was added to a solution of 100% 1,5-PD obtained through distillation, and 35% hydrochloric acid was then added for neutralization to prepare a solution of 12% by weight 1,5-PD hydrochloride with a pH of 7.

(2) Pretreatment of resin; A resin tower was filled with the weakly acidic cation exchange resin, and 10 RV of 0.2N HCl, 10 RV of ultrapure water, 10 RV of 1N NaOH, and 10 RV of ultrapure water were applied to the resin tower to regenerate the resin as a $Na^+$ type resin.

(3) Examination of adsorption amount; The solution of 1,5-PD hydrochloride prepared in (1) was applied in a downflow mode (the solution was supplied to an upper portion of the resin tower and drawn from a lower portion) while loading 260 g/L-Resin to the pretreated resin in (2). Thus, 1,5-PD was adsorbed on the resin. After applying the test solution, ultrapure water was applied to each of the resin towers by the flowing method that was the same as in the adsorption to remove unabsorbed 1,5-PD from each of the resin towers.

(4) 2N NaOH, 2N potassium hydroxide, and 4N aqueous ammonia were applied to the resin towers at 20° C. in an upflow mode (the liquid was supplied to the lower portion of the resin tower and drawn from the upper portion), respectively, and elution of 1,5-PD and breakthrough of sodium were each confirmed.

Figure 18:
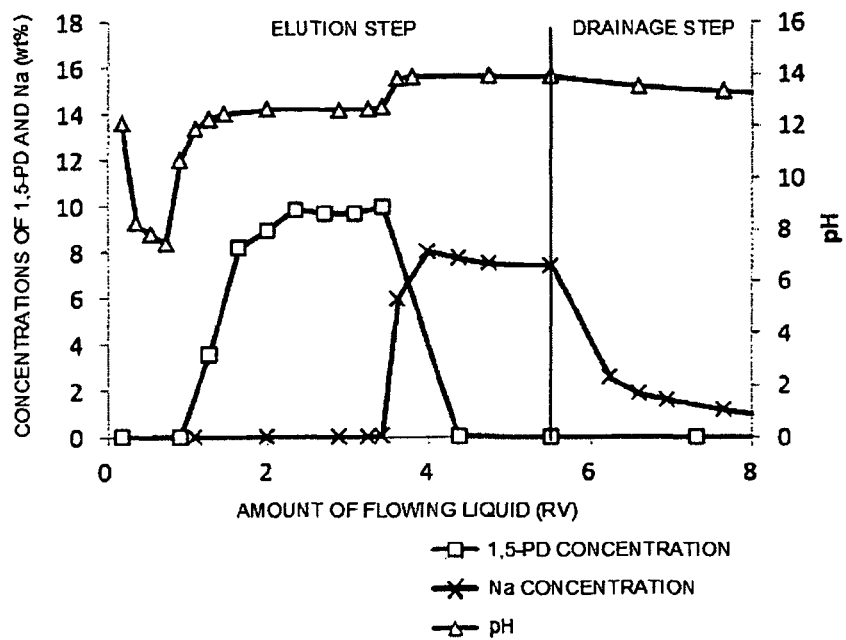
FIG. 18 shows an elution curve when a 1,5-PD hydrochloride solution was applied in the downflow mode to a weakly acidic cation exchange resin, ultrapure water was then applied to a resin tower to remove unabsorbed 1,5-PD, and 2N NaOH was then applied in the upflow mode (Example 9).

FIG. 18 shows an elution curve when the 1,5-PD hydrochloride solution was applied in the downflow mode to the weakly acidic cation exchange resin, ultrapure water was then applied to the resin tower to remove 1,5-PD that was not adsorbed on the resin, and 2N NaOH was passed in the upflow mode.

Figure 19:
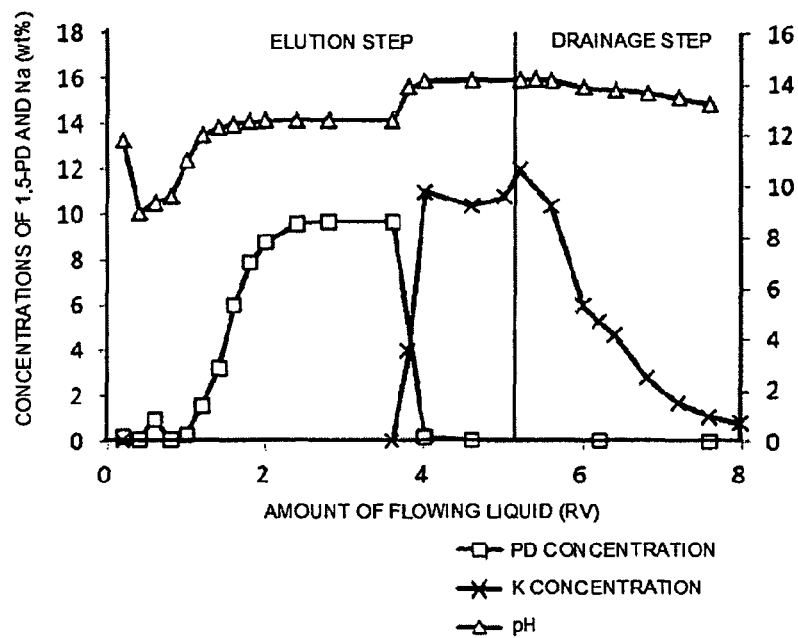
FIG. 19 shows an elution curve when a 1,5-PD hydrochloride solution was applied in the downflow mode to a weakly acidic cation exchange resin, ultrapure water was then applied to a resin tower to remove unabsorbed 1,5-PD, and 2N KOH was then applied in the upflow mode (Example 9).

FIG. 19 shows an elution curve when the 1,5-PD hydrochloride solution was applied in the downflow mode to the weakly acidic cation exchange resin, ultrapure water was then applied the resin tower to remove unabsorbed 1,5-PD, and 2N KOH was applied in the upflow mode.

Figure 20:
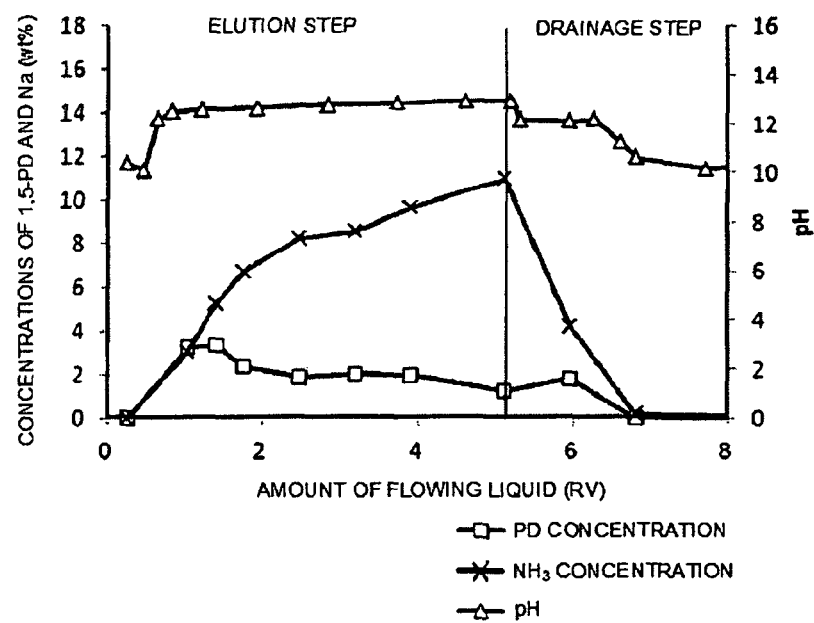
FIG. 20 shows an elution curve when a 1,5-PD hydrochloride solution was applied in the downflow mode to a weakly acidic cation exchange resin, ultrapure water was then applied to a resin tower to remove unabsorbed 1,5-PD, and 4N $NH_4OH$ was then applied in the upflow mode (Example 9).

FIG. 20 shows an elution curve when the 1,5-PD hydrochloride solution was applied in the downflow mode to the weakly acidic cation exchange resin, ultrapure water was then applied to the resin tower to remove unabsorbed 1,5-PD, and 4N $NH_4OH$ was applied in the upflow mode.

In all the eluents, elution of 1,5-PD is possible. In the elution using sodium hydroxide or potassium hydroxide, the elution of 1,5-PD is almost completed and breakthrough of sodium or potassium then starts. Therefore, a solution of 1,5-PD in a free form in which the concentration of 1,5-PD is high and contamination with the eluent is suppressed can be obtained. In the elution using aqueous ammonia, breakthrough of ammonia starts with onset of elution of 1,5-PD, and the eluent contaminates the eluted liquid of 1,5-PD. This is considered because the alkalinity of aqueous ammonia is lower than those of sodium hydroxide and potassium hydroxide.

Example 10 Selection of Elution Temperature

Elution Step: Selection of Temperature of Eluent (1) Preparation of test solution; Water was added to a solution of 100% 1,5-PD obtained through distillation, and 35% hydrochloric acid was then added for neutralization to prepare a solution of 12% by weight 1,5-PD hydrochloride with a pH of 7.

(2) Pretreatment of resin; A resin tower was filled with the weakly acidic cation exchange resin, and 10 RV of 0.2N HCl, 10 RV of ultrapure water, 10 RV of 1N NaOH, and 10 RV of ultrapure water were applied to the resin tower to regenerate the resin as a $Na^+$ type resin.

(3) Examination of adsorption amount; The solution of 1,5-PD hydrochloride prepared in (1) was applied in a downflow mode (the solution was supplied to an upper portion of the resin tower and drawn from a lower portion) while loading 260 g/L-Resin to the pretreated resin in (2). Thus, 1,5-PD was adsorbed on the resin. After applying the test solution, ultrapure water was applied to each of the resin towers by the flowing method that was the same as in the adsorption to remove unabsorbed 1,5-PD from each of the resin towers.

(4) 2N NaOH adjusted at each of 20° C. and 40° C. was applied to the resin tower in an upflow mode (the liquid was supplied to the lower portion of the resin tower and drawn from the upper portion), and elution of 1,5-PD and breakthrough of sodium were each confirmed.

Figure 21:
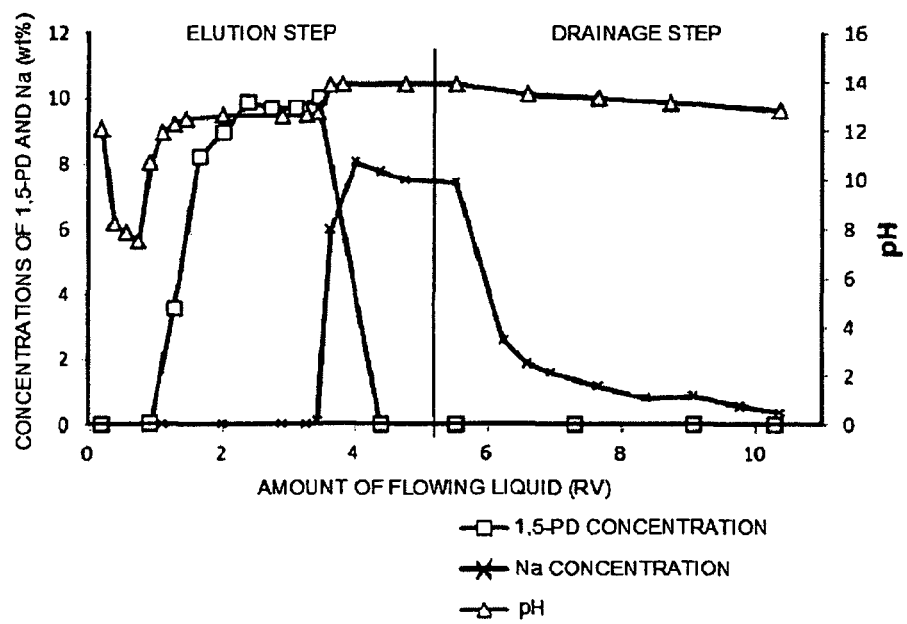
FIG. 21 shows an elution curve when a 1,5-PD hydrochloride solution was applied in the downflow mode to a weakly acidic cation exchange resin, ultrapure water was then applied to a resin tower to remove unabsorbed 1,5-PD, and 2N NaOH at 20° C. was then applied in the upflow mode (Example 10).

FIG. 21 shows an elution curve when the 1,5-PD hydrochloride solution was applied in the downflow mode to the weakly acidic cation exchange resin, ultrapure water was then applied to the resin tower to remove unabsorbed 1,5-PD, and 2N NaOH at 20° C. was applied in the upflow mode.

Figure 22:
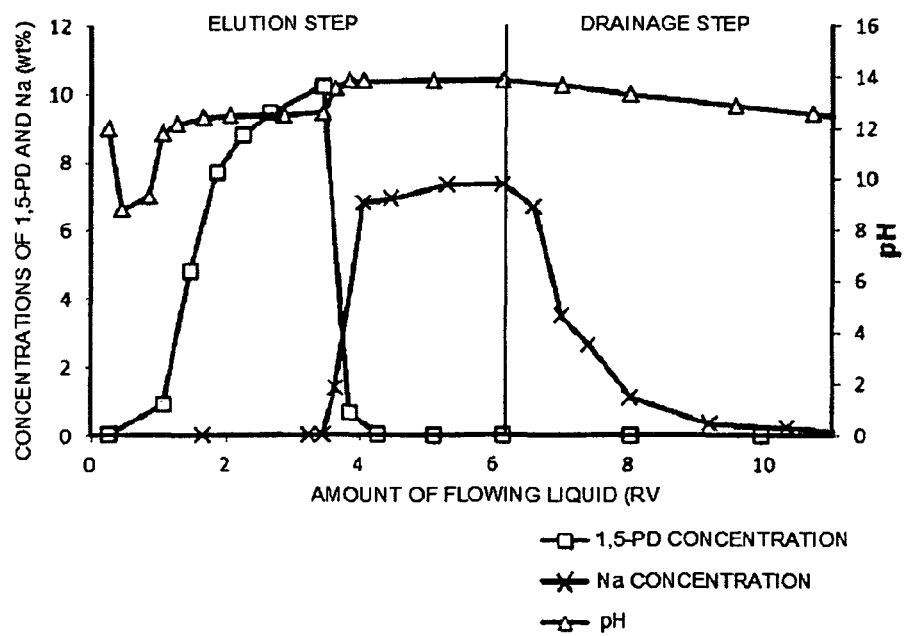
FIG. 22 shows an elution curve when a 1,5-PD hydrochloride solution was applied in the downflow mode to a weakly acidic cation exchange resin, ultrapure water was then applied to a resin tower to remove 1,5-PD, and 2N NaOH at 40° C. was then applied in the upflow mode (Example 10).

FIG. 22 shows an elution curve when the 1,5-PD hydrochloride solution was applied in the downflow mode to the weakly acidic cation exchange resin, ultrapure water was then applied to the resin tower to remove unabsorbed 1,5-PD, and 2 N NaOH at 40° C. was applied in the upflow mode.

At all the eluent temperatures, elution of 1,5-PD is possible. The exchange efficiency of 1,5-PD with the eluent is improved with an increase in the eluent temperature, and a solution of 1,5-PD in a free form in which contamination with the eluent is decreased can be obtained.

Example 11 Selection of Concentration of Eluent in Upflow Flowing Mode

Elution Step: Selection of Concentration of Eluent in Upflow Flowing Mode (1) Preparation of test solution; Water was added to a solution of 100% 1,5-PD obtained through distillation, and 35% hydrochloric acid was then added for neutralization to prepare a solution of 8% by weight 1,5-PD hydrochloride with a pH of 5.

(2) Pretreatment of resin; A resin tower was filled with the weakly acidic cation exchange resin, and 10 RV of 0.2N HCl, 10 RV of ultrapure water, 10 RV of 1N NaOH, and 10 RV of ultrapure water were applied to the resin tower to regenerate the resin as a $Na^+$ type resin.

(3) Examination of adsorption amount; The solution of 1,5-PD hydrochloride prepared in (1) was applied in a downflow mode (the solution was supplied to an upper portion of the resin tower and drawn from a lower portion) while loading 360 g/L-Resin to the pretreated resin in (2). Thus, 1,5-PD was adsorbed on the resin. After applying the test solution, ultrapure water was applied to each of the resin towers by the flowing method that was the same as in the adsorption to remove unabsorbed 1,5-PD from each of the resin towers.

(4) 1N, 2N, and 4N NaOH were applied to the resin towers in an upflow mode (the liquid was supplied to the lower portion of the resin tower and drawn from the upper portion), respectively, and elution of 1,5-PD and breakthrough of sodium were each confirmed.

Figure 23:
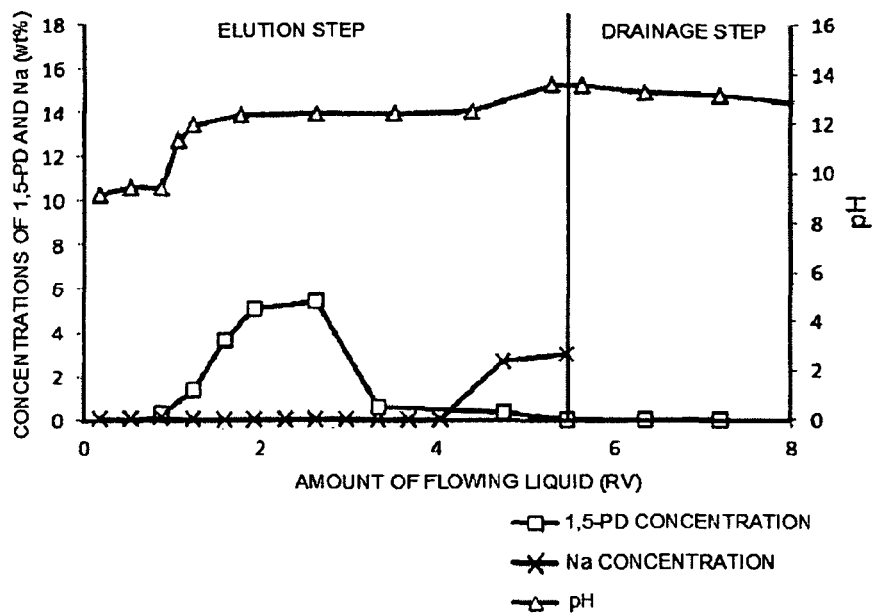
FIG. 23 shows an elution curve when a 1,5-PD hydrochloride solution was applied in the downflow mode to a weakly acidic cation exchange resin, ultrapure water was then applied to a resin tower to remove unabsorbed 1,5-PD, and 1N NaOH was then applied in the upflow mode (Example 11).

FIG. 23 shows an elution curve when the 1,5-PD hydrochloride solution was applied in the downflow mode to the weakly acidic cation exchange resin, ultrapure water was then applied to the resin tower to remove unabsorbed 1,5-PD, and 1N NaOH was applied in the upflow mode.

Figure 24:
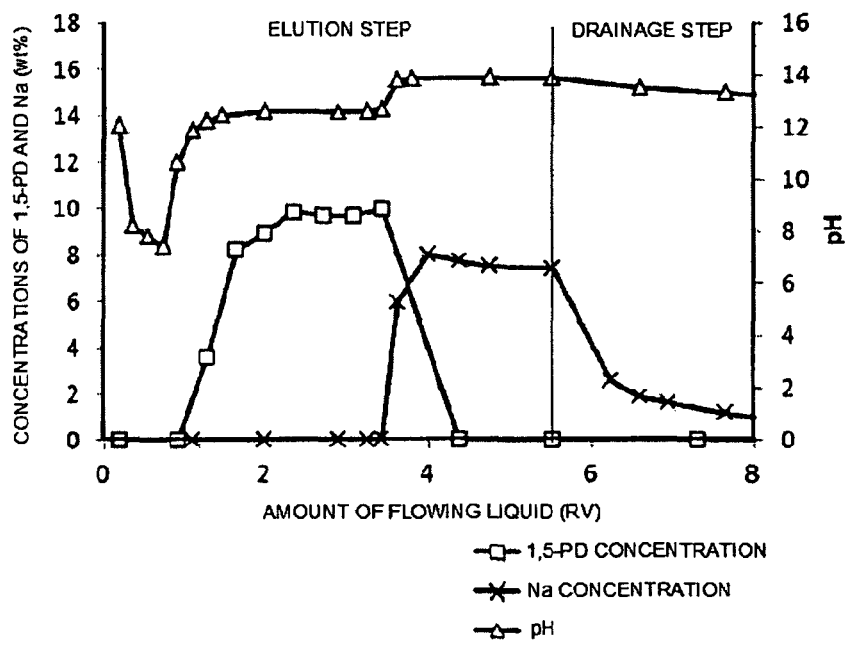
FIG. 24 shows an elution curve when a 1,5-PD hydrochloride solution was applied in the downflow mode to a weakly acidic cation exchange resin, ultrapure water was then applied to a resin tower to remove unabsorbed 1,5-PD, and 2N NaOH was then applied in the upflow mode (Example 11).

FIG. 24 shows an elution curve in a case where the 1,5-PD hydrochloride solution was applied in the downflow mode to the weakly acidic cation exchange resin, ultrapure water was then applied to the resin tower to remove unabsorbed 1,5-PD, and 2N NaOH was applied in the upflow mode.

Figure 25:
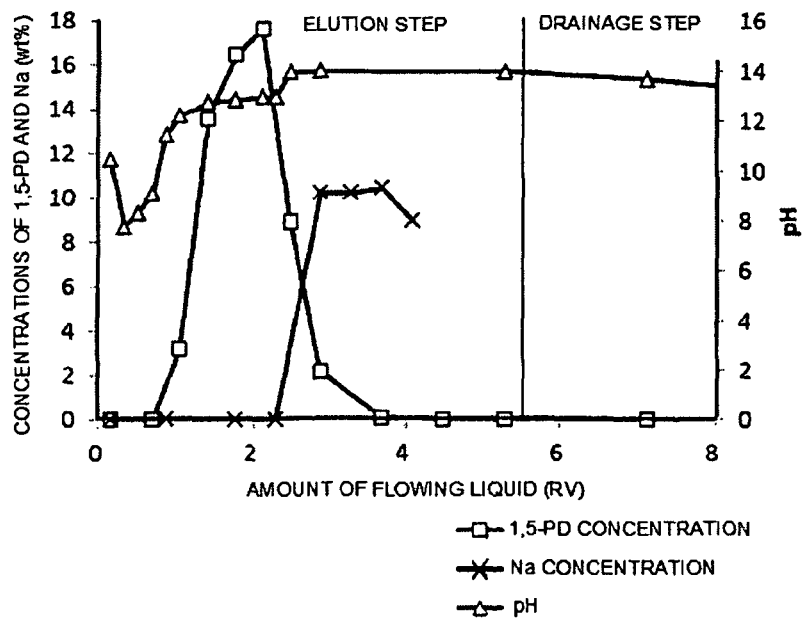
FIG. 25 shows an elution curve when a 1,5-PD hydrochloride solution was applied in the downflow mode to a weakly acidic cation exchange resin, ultrapure water was then applied to a resin tower to remove unabsorbed 1,5-PD, and 4N NaOH was then applied in the upflow mode (Example 11).

FIG. 25 shows an elution curve when the 1,5-PD hydrochloride solution was applied in the downflow mode to the weakly acidic cation exchange resin, ultrapure water was then applied to the resin tower to remove unabsorbed 1,5-PD, and 4N NaOH was applied in the upflow mode.

At all the eluent temperatures, elution of 1,5-PD is possible.

The concentration of 1,5-PD to be collected can be largely increased with an increase in the concentration of the eluent. The concentrations of 1,5-PD in these cases are 6% by weight, 10% by weight, and 18% by weight, respectively. Under all the conditions, the exchange efficiency of 1,5-PD with the eluent can be maintained, and a solution of 1,5-PD in a free form in which contamination with the eluent is decreased can be obtained.

Example 12 An Example of Conditions Suitable for Industrialization by a Combination of Aspects of the Present Invention Selection of One Example of Operating Process Suitable for Industrialization In production of a solution of 1,5-PD in a free form in the present invention, a process at high efficiency and high degree of purification is established. In this Example, an operation process that is established by combination of resin process parameters in the adsorption and elution selected in the respective Examples and is suitable for industrialization is described.

(1) Preparation of test solution; Water was added to a solution of 100% 1,5-PD obtained through distillation, and 35% hydrochloric acid was then added for neutralization to prepare a solution of 7.5% by weight 1,5-PD hydrochloride with a pH of 7.

(2) Pretreatment of resin; A resin tower was filled with the weakly acidic cation exchange resin, and 10 RV of 0.2N HCl, 10 RV of ultrapure water, 10 RV of 1N NaOH, and 10 RV of ultrapure water were applied to the resin tower to regenerate the resin as a $Na^+$ type resin.

(3) Adsorption step; The solution of 1,5-PD hydrochloride prepared in (1) was applied in a downflow mode (the solution was supplied to an upper portion of the resin tower and drawn from a lower portion) while a loading of 257 g L-Resin was applied to the pretreated resin in (2). Thus, 1,5-PD was adsorbed on the resin. After applying the test solution, About 4 RV of ultrapure water was applied to the resin tower by the flowing method that was the same as in the adsorption to remove unabsorbed 1,5-PD from the resin tower.

(4) Elution step; 2N NaOH was applied to the resin tower that adsorbs 1,5-PD in (3) in an upflow mode (the liquid was supplied to the lower portion of the resin tower and drawn from the upper portion), and elution of 1,5-PD and breakthrough of sodium were each confirmed.

Figure 26:
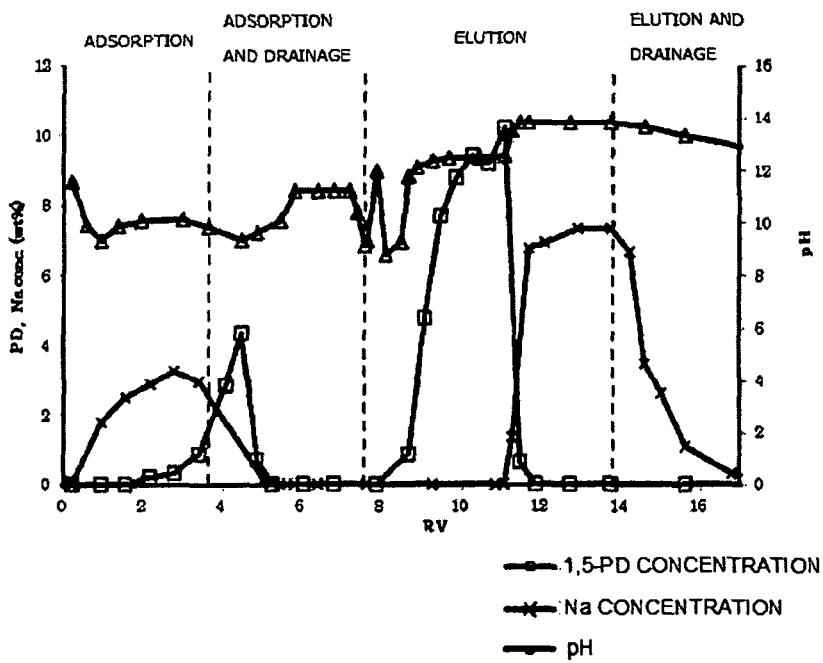
FIG. 26 shows one example of an adsorption and elution curve under conditions suitable for industrialization.

FIG. 26 shows one example of adsorption and elution curve under the operation condition suitable for industrialization.

The adsorption amount of 1,5-PD on the resin is 212 g/L-Resin. The amount of 1,5-PD that could be collected as the eluent is 207 g/L-Resin. Therefore, adsorbed 1,5-PD can be completely collected and a counter ion can be reduced.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing 1,5-pentanediamine in a free form from a salt of 1,5-pentanediamine comprising:
    A) applying a solution of a salt of 1,5-pentanediamine to an ion exchange resin column in a downflow mode thereby allowing adsorption of 1,5-pentanediamine in free form onto the column; and
    B) applying an eluent solution to the column in an upflow mode, thereby eluting a solution of the 1,5-pentanediamine in free form from the column, wherein the eluent solution is sodium hydroxide or potassium hydroxide,
    wherein the salt of 1,5-pentanediamine is a hydrochloride or a sulfate.

2. The method according to claim 1, wherein the ion exchange resin is a weakly acidic cation exchange resin.

3. The method according to claim 1, wherein the solution of the salt of 1,5-pentanediamine has a pH of 3 to 10.

4. The method according to claim 1, wherein the solution of the salt of 1,5-pentanediamine has a temperature of 15 to 60° C.

5. The method according to claim 1, wherein the eluent solution has a temperature of 15 to 60° C.

6. The method according to claim 1, wherein the eluent solution has a concentration of 0.5 N to 4 N.

* * * * *